United States Patent
Garrison et al.

(10) Patent No.: US 7,101,182 B2
(45) Date of Patent: Sep. 5, 2006

(54) DENTAL APPARATUS

(75) Inventors: Thomas Garrison, Spring Lake, MI (US); Robert Anderson, Grand Haven, MI (US); David Allen Dunlap, Portage, MI (US); Willard L Van Harn, Holland, MI (US)

(73) Assignee: Garrison Dental Solutions, Spring Lake, MI (US)

( * ) Notice: Subject to any disclaimer, the term of this patent is extended or adjusted under 35 U.S.C. 154(b) by 369 days.

(21) Appl. No.: 10/200,665

(22) Filed: Jul. 22, 2002

(65) Prior Publication Data

US 2004/0014004 A1 Jan. 22, 2004

(51) Int. Cl.
*A61G 3/06* (2006.01)

(52) U.S. Cl. .......................................... 433/125; 433/82
(58) Field of Classification Search ................. 433/125, 433/82, 83, 85, 87
See application file for complete search history.

(56) References Cited

U.S. PATENT DOCUMENTS

| | | | |
|---|---|---|---|
| 2,300,828 A | 11/1942 | Goldenberg | |
| 2,400,912 A | 5/1946 | Britt et al. | |
| 2,707,329 A | 5/1955 | Costoff | |
| 2,738,528 A | 3/1956 | Fridge, Sr. | |
| 3,389,468 A | 6/1968 | Lewis et al. | |
| 3,691,636 A | 9/1972 | Deuschle | |
| 3,727,313 A | 4/1973 | Graham | |
| 3,769,707 A | 11/1973 | Condon | |
| 3,775,849 A | 12/1973 | Condon | |
| 4,259,071 A | 3/1981 | Warden et al. | |
| 4,266,933 A | 5/1981 | Warden et al. | |
| 4,581,022 A | * 4/1986 | Leonard et al. ............. | 604/229 |
| 5,062,796 A | 11/1991 | Rosenberg | |
| 5,209,658 A | 5/1993 | Brahler | |
| 5,360,339 A | 11/1994 | Rosenberg | |
| 5,374,189 A | 12/1994 | Mendoza | |
| 5,380,202 A | 1/1995 | Brahler | |
| 5,626,473 A | 5/1997 | Muhlbauer et al. | |
| 5,642,994 A | 7/1997 | Chipian et al. | |
| 5,642,995 A | 7/1997 | Balloy | |
| 5,645,426 A | 7/1997 | Grim et al. | |
| 5,683,247 A | 11/1997 | Balloy | |
| 5,690,488 A | 11/1997 | Spinello | |
| 5,707,234 A | 1/1998 | Bender | |
| 5,718,582 A | 2/1998 | Quinn et al. | |
| 5,730,593 A | 3/1998 | Mack | |
| 5,730,595 A | 3/1998 | Bailey | |
| 5,775,905 A | 7/1998 | Weissenfluh et al. | |
| 5,797,744 A | 8/1998 | Rosenberg | |
| 5,871,353 A | 2/1999 | Pierce et al. | |
| 5,876,203 A | 3/1999 | Bailey | |
| 5,902,107 A | 5/1999 | Lowell | |
| 6,257,886 B1 | 7/2001 | Warner | |

* cited by examiner

*Primary Examiner*—Kevin Shaver
*Assistant Examiner*—Candice C. Stokes
(74) *Attorney, Agent, or Firm*—Watson IP Group; Jovan N. Jovanovic (57) ABSTRACT

A prophy angle comprising a body, a drive system, and a paste feed assembly. The body includes a cylinder and a head portion associated with the cylinder. The drive system extends through the body and includes a drive shaft assembly and a cup shaft assembly. The drive shaft assembly extends through the cylinder. The cup shaft assembly extends through the head portion. The cup shaft assembly is coupled to the drive shaft assembly and further includes a prophy cup disposed at one end thereof. The prophy cup is in fluid communication with the body. The paste feed assembly includes a piston assembly and a piston movement assembly. The piston movement assembly includes a handle member. The handle member includes a second end associated with the piston assembly, a first end distally spaced therefrom and a pivot point positioned therebetween. Rotation of the first end of the handle member about the pivot point rotates the second end, moving the piston assembly relative to the body, to, in turn, direct paste positioned within the body to the prophy cup.

5 Claims, 11 Drawing Sheets

DENTAL APPARATUS

BACKGROUND OF THE INVENTION

1. Field of the Invention

The invention relates in general to a dental apparatus, and more particularly, to a dental polishing apparatus, i.e., a prophy angle, which is configured to facilitate the dispensing of paste from within the apparatus into a prophy cup upon selective actuation by a user.

2. Background Art

The use of polishing devices by dental practitioners is known in the art. Generally, such devices are termed prophy angles, and include a prophy cup which rotates about an axis. The prophy cup includes an inner cavity into which a polishing paste is inserted. Once the polishing paste has been applied to the prophy cup, the prophy cup is rotated and introduced to the teeth of a patient. The rotation of the prophy cup directs the paste along the surface of the teeth, and, by way of abrasion, serves to polish the teeth of the patient.

While the use of prophy angles has been known in the art for several years, there still exist a number of deficiencies associated with such prophy angle use. For example, in certain embodiments, the prophy angle may comprise a reusable device to which separate prophy cups are attached. Once attached, the paste is applied to the prophy cup from a separate, small container. However, use of such reusable devices may introduce health and sanitation risks when transferred from one patient to another, despite the changing of the prophy cup. Therefore, for sanitary purposes, the preferable embodiment of the prophy angle comprises a disposable, single-use device which is utilized for a single patient and is then discarded. However, while the use of disposable devices has been developed, the paste is nevertheless manually applied from a separate container, which may be inconvenient for the dental practitioner. To remedy this situation, certain new embodiments of prophy angles now incorporate paste dispensing means integrally associated with the prophy angle. While such embodiments exist, certain drawbacks have precluded the widespread acceptance and use of such devices.

Certain devices have included automatic feed mechanisms which include a particular feed rate when the device is operating. Often times, however, such systems are not reliable and the user has no ability to control the application of paste.

Other devices have provided a manually manipulatable application means. However, with many such manually manipulatable application means, it is quite difficult to control the quantity of paste that is applied. As such, often times, too little or too much paste is applied.

To overcome such deficiencies, other designs have relied on manually actuatable application means which provide a particular quantity of paste each time they are actuated. As such, the user can control the quantity of paste that is directed to a prophy cup. While such solutions have been an improvement, they nevertheless include various drawbacks. In particular, the actuation mechanisms and assemblies may be difficult to actuate due, in part, to the relatively small size of the prophy angles and, in turn, the actuating mechanisms. In addition, the actuation mechanisms and assemblies may be actuatable only when the prophy angles are disposed in a particular orientation. As the dental practitioner is constantly manipulating a prophy angle in a variety of orientations during polishing, it has proven difficult to actuate the actuation mechanisms and assemblies while such prophy angles are in use.

As a result, it is an object of the present invention to provide a prophy angle which includes a paste feed assembly that overcomes the deficiencies and/or drawbacks identified above.

SUMMARY OF THE INVENTION

The present invention is directed to a prophy angle. The prophy angle of the present invention preferably comprises a body, a drive system, and a paste feed assembly. The body includes a cylinder and a head portion associated with the cylinder. The drive system extends through the body and includes a drive shaft assembly and a cup shaft assembly. The drive shaft assembly extends through the cylinder. The cup shaft assembly extends through the head portion. The cup shaft assembly is coupled to the drive shaft assembly and further includes a prophy cup disposed at one end thereof. The prophy cup is in fluid communication with the body. The paste feed assembly includes a piston assembly and a piston movement assembly. The piston assembly is disposed within the body. The piston movement assembly includes a handle member. The handle member includes a second end associated with the piston assembly, a first end distally spaced therefrom and a pivot point positioned therebetween. Rotation of the first end of the handle member about the pivot point rotates the second end, moving the piston assembly relative to the body, to, in turn, direct paste positioned within the body to the prophy cup.

In a preferred embodiment, the piston assembly further comprises a front face and a trailing surface. The trailing surface further includes a plurality of teeth. The piston movement assembly further includes a piston engagement member. The piston engagement member further includes at least one tooth engagement finger. The at least one tooth engagement finger is capable of engaging at least one tooth of the trailing surface of the piston assembly. In such an embodiment, the piston engagement member is coupled to the handle member such that movement of the handle member in a first direction imparts movement to the piston engagement member in a first direction, and movement of the handle member in a second direction imparts movement of the piston engagement member in a second direction.

Additionally, in such an embodiment, the teeth of the trailing surface and the at least one tooth engagement finger are configured such that movement of the at least one tooth engagement finger in a first direction imparts movement of the piston assembly in a first direction, and movement of the at least one tooth engagement finger in a second direction translates the at least one tooth engagement finger relative to the teeth of the trailing surface.

In one such embodiment, the piston engagement member further comprises a tube member from which the at least one tooth engagement finger extends. The tube member further includes at least one follower associated therewith. The handle member further includes at least one cam surface associated with the second end thereof. The at least one cam surface interfaces with the at least one follower, to, in turn, impart slidable movement of the piston engagement member within the cylinder of the body.

In another preferred embodiment, the at least one tooth engagement member further comprises a plurality of teeth engagement members.

In yet another such preferred embodiment, the tube member further includes at least two followers associated therewith. Additionally, the handle member further includes at least two cam surfaces associated with the second end thereof. Each of the at least two cam surfaces cooperate with a respective follower to, in turn, impart slidable movement of the piston engagement member within the cylinder of the body.

In another preferred embodiment, the at least two followers are positioned on opposing sides of the tube member.

In yet another preferred embodiment, the trailing surface includes a plurality of teeth positioned sequentially along the length thereof. The at least one tooth engagement finger is configured such that movement thereof in the second direction translates the at least one tooth engagement finger sequentially from a first tooth to an adjacent tooth in a direction away from the front face of the piston assembly.

The present invention is further directed to a prophy angle which includes a body, a drive system, and a paste feed assembly. The drive system extends through the body and includes a rotatably positioned prophy cup disposed at one end thereof. The paste feed assembly includes a piston assembly and a piston movement assembly. The piston assembly is disposed within the body. The piston movement assembly includes a handle member. The handle member includes a first end, a second end, and a pivot point positioned therebetween. The pivot point is coupled to the body. The handle member is rotatable from a first position to a second position, wherein the rotation of the handle member from a first position to a second position imparts movement to the piston assembly in a first direction relative to the body.

In one preferred embodiment, the piston assembly remains substantially stationary upon rotation of the handle member from the second position to the first position.

In another preferred embodiment, successive cycles of the handle member from the first position to the second position and back to the first position imparts incremental movement of the piston assembly in a first direction relative to the body.

In yet another preferred embodiment, the invention further includes a paste positioned within the body, between the piston assembly and the prophy cup.

In another aspect of the invention, the prophy angle comprises a body, a drive system, a piston assembly, a paste, and a piston movement assembly. The drive system extends through the body and includes a rotatably positioned prophy cup disposed at one end thereof. The prophy cup includes an opening in fluid communication with the body. The piston assembly is disposed within the body and cooperates with the body to define a cavity. The paste is disposed within the cavity. The piston movement assembly includes a handle member. The handle member includes a first end, a second end, and a pivot point positioned therebetween. The pivot point is coupled to the body. The handle member is cyclically rotatable: from a first position to a second position and back to the first position. The cyclical rotation of the handle member imparts movement of the piston assembly, to, in turn, reduce the cavity, and force paste from within the cavity into the prophy cup.

In one preferred embodiment, the prophy cup includes an inner cavity. The reduction of the cavity corresponds to a volume of the inner cavity of the prophy cup.

In another preferred embodiment, the piston movement assembly further includes a piston engagement member coupled to the handle member. The piston movement assembly is capable of coupling with the piston assembly upon movement thereof in a first direction, and is capable of substantial independent movement relative to the piston assembly upon movement thereof in a second direction.

BRIEF DESCRIPTION OF THE DRAWINGS

The invention will now be described with reference to the drawings wherein.

DETAILED DESCRIPTION OF THE INVENTION

While this invention is capable of embodiment in many different forms, there is shown in the drawings and will be described herein in detail, one specific embodiment with the understanding that the present disclosure is to be considered as an exemplification of the principles of the invention and is not intended to limit the invention to the embodiment illustrated.

It will be understood that like or analogous elements and/or components, referred to herein, are identified throughout the drawings by like reference characters. In addition, it will be understood that the drawings are merely representations, and some of the components may have been distorted from actual scale for purposes of pictorial clarity.

Figure 9:
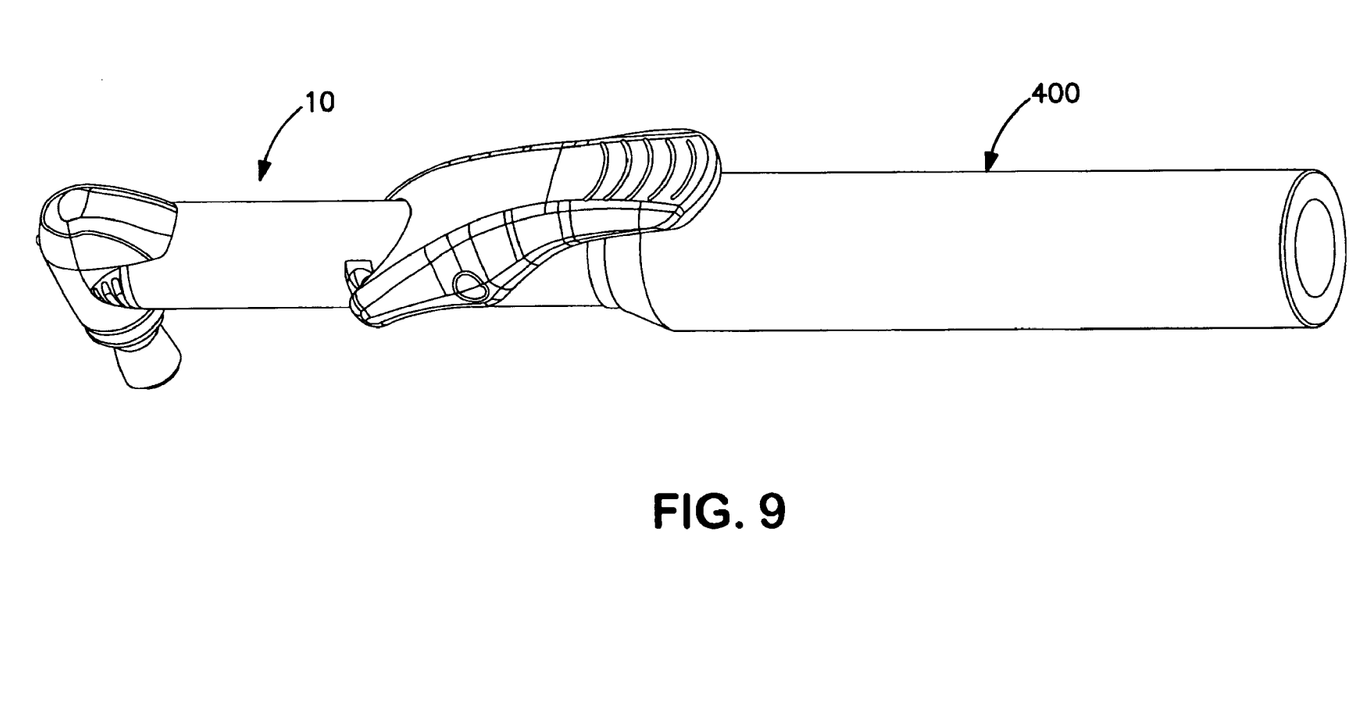
FIG. 9 of the drawings comprises a perspective view of a dental apparatus in accordance with the present invention, showing, in particular, attachment of same to a dental hand piece.

Dental apparatus 10 (commonly referred to as a prophy angle) is shown in FIGS. 1 through 4 and 6 as comprising body 12, drive system 14, and paste feed assembly 16. As shown in FIG. 9, prophy angle 10 is designed for use with low speed dental hand piece 400 commonly found in a dental office. Generally, such prophy angles are formed entirely from plastic and/or rubber materials, which render the apparatus disposable. Of course, it is likewise contemplated that the device may be reusable.

Figure 3:
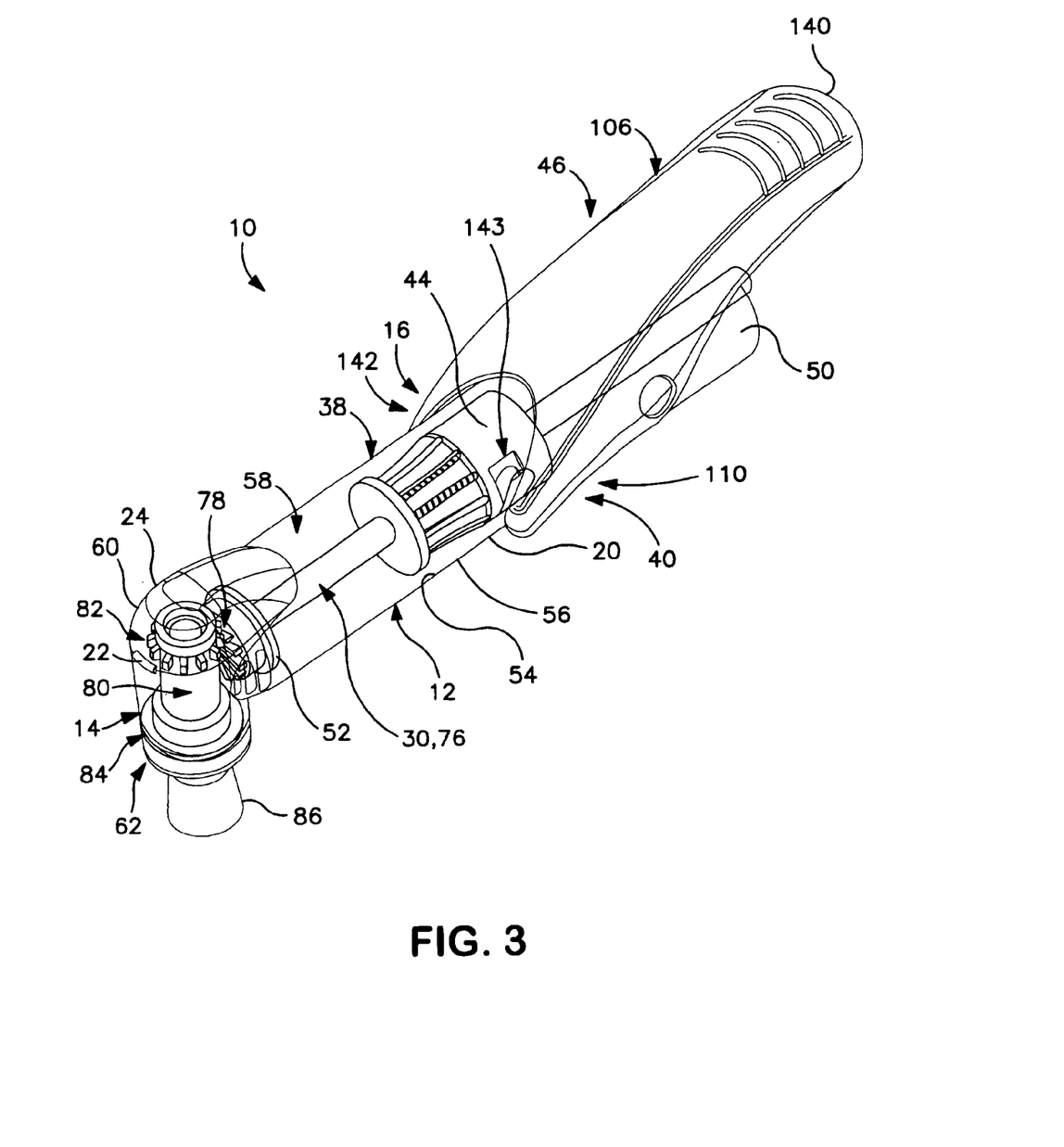
FIG. 3 of the drawings comprises a phantom perspective view of a dental apparatus in accordance with the present invention, showing, in particular, internal propulsion components.
Figure 4:
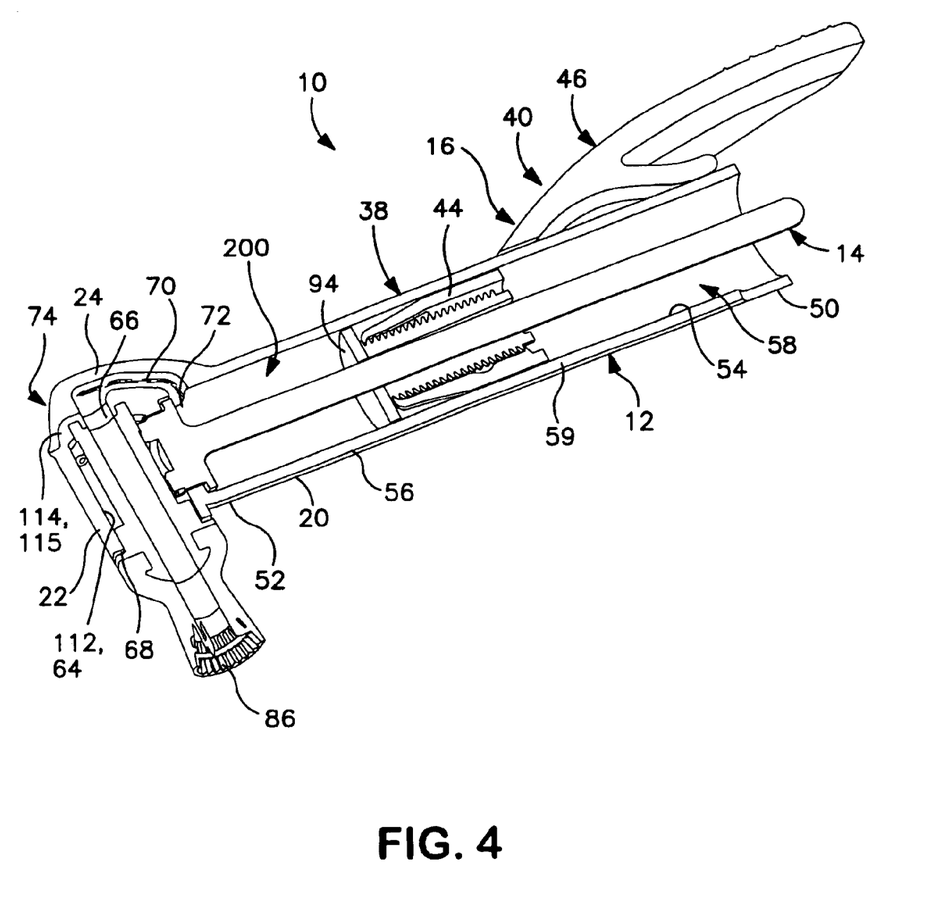
FIG. 4 of the drawings comprises a cross-sectional view of a dental apparatus in accordance with the present invention.
Figure 5:
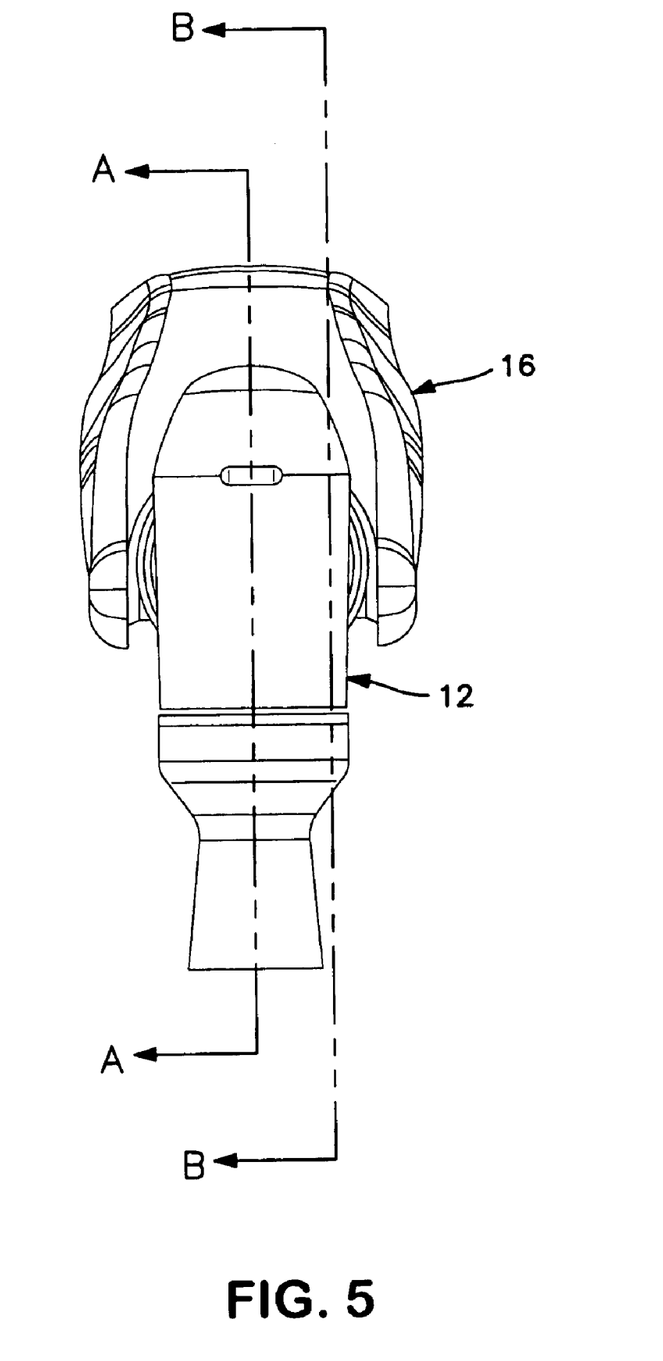
FIG. 5 of the drawings comprises a front plan view of a dental apparatus in accordance with the present invention.

Body 12 is shown in FIGS. 3 and 4 as comprising cylinder 20, head portion 22, and cap 24. Preferably, body 12 is sized to comfortably be retained and manipulated by a single hand of a user. In particular, and as shown in more detail in FIG.

6, cylinder 20 includes first end 50, second end 52, inner surface 54, outer surface 56, opposing slots (such as slot 143 in FIGS. 3 and 6), and cross-sectional configuration 58. Inner surface 54 extends from first end 50 to second end 52 and generally comprises a uniform circular cross-sectional configuration 58. The inner and outer surfaces can be substantially collinear, defining cylinder wall 59 of a substantially uniform thickness. The cross-sectional configuration 58 may comprise a variety of different shapes, including, but not limited to, any geometric shapes (i.e., triangular, rectangular, multi-sided, circular, oval, elliptical, etc.).

Figure 6:
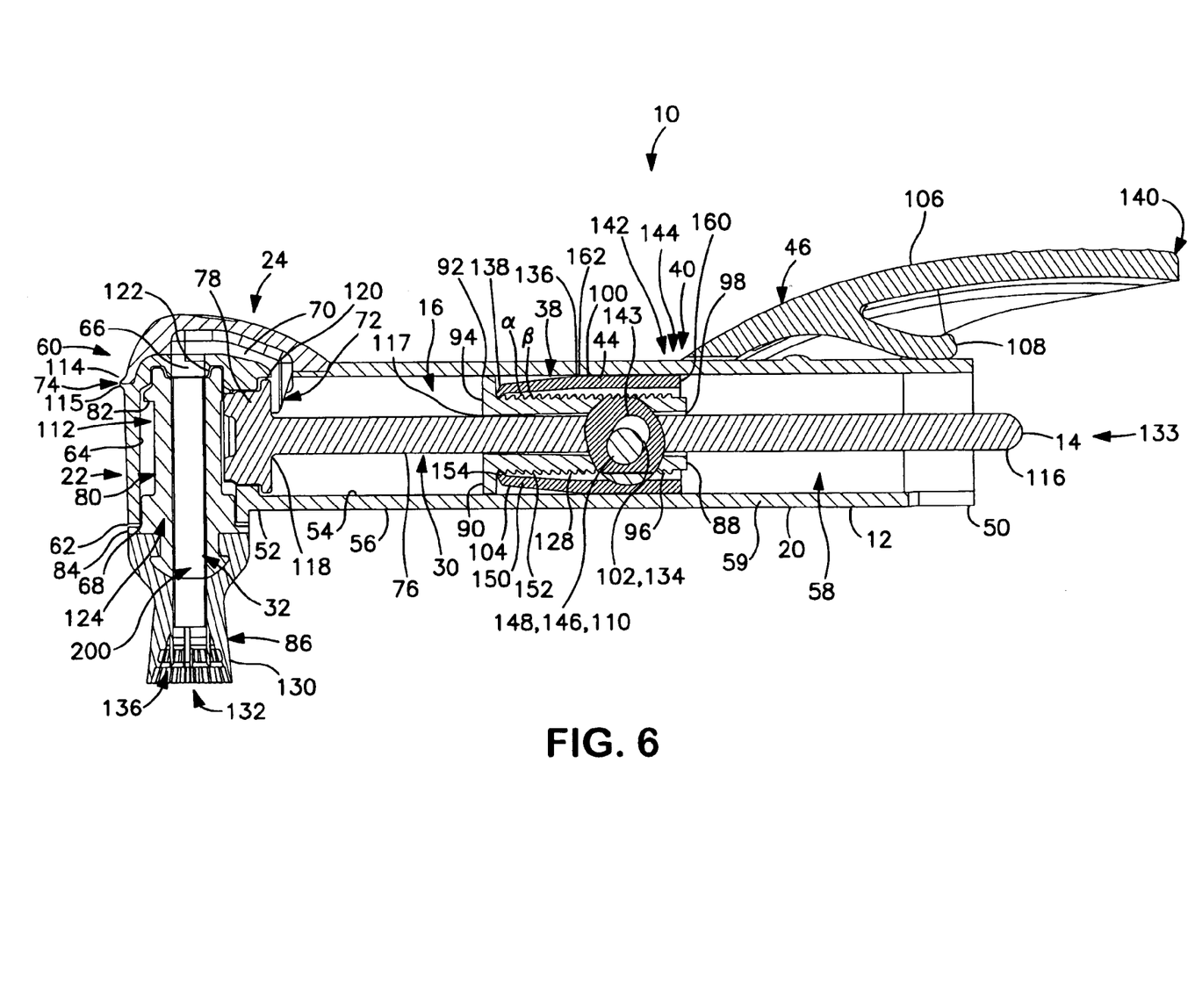
FIG. 6 of the drawings comprises a cross-sectional view of a dental apparatus in accordance with the present invention.

As shown in FIG. 6, opposing slots, such as slot 143, are positioned on opposing sides of cylinder 20 and extend through cylinder 20 from outer surface 56 to inner surface 54. It will be understood that one opposing slot (not shown) is positioned about 180 degrees on the other side of the cylinder as the other opposing slot, such as slot 143. Preferably, the slots are substantially perpendicular to the general axis of cylinder 20. Of course, different slots having different positions and having different orientations are likewise contemplated for use. In addition, it is contemplated that one embodiment of the invention may include only a single slot 143.

Head portion 22 is shown in FIG. 6 as comprising top end 60, bottom end 62, inner surface 64, bore 66, and opening 68. Top end 60 of head portion 22 is associated with second end 52 of cylinder 20. Inner surface 64 defines cavity 112. Cavity 112 is in communication with cylinder 20. Additionally, bore 66 is in fluid communication with cavity 112. Opening 68 is likewise associated with cavity 112 and provides egress therefrom. Preferably, cylinder 20 and head portion 22 are integrally molded together as a single component, however, other structures are likewise contemplated for use. Additionally, while the cylinder and the head portion are generally positioned at approximately 90 degrees relative to each other, it is contemplated that the two may be disposed at any number of different angles relative to each other.

Cap 24 is shown in FIG. 6 as comprising passage 70, interfacing lip 72, and attachment assembly 74. Cap 24 is associated with top end 60 of head portion 22. Cap 24 is positioned such that passage 70 is positioned to provide communication between cylinder 20 and bore 66. In addition, interfacing lip 72 extends into cylinder 20 proximate second end 52 thereof. As will be explained, interfacing lip 72 is configured to retain a drive shaft assembly in a properly assembled configuration.

Attachment assembly 74 includes slots 114 associated with head portion 22 and cylinder 20 and tabs 115 associated with cap 24. The slots and tabs correspond and cooperate to retain cap 24 in an engaged orientation relative to the cylinder and the head portion. It is contemplated that the cylinder, head portion, and cap may be integrally molded into a single component. In addition, it is contemplated that various structures may be dimensionally or structurally modified by one of ordinary skill in the art without departing from the function thereof.

Drive system 14 is shown in FIGS. 3 and 6 as comprising drive shaft assembly 30 and cup shaft assembly 32. Drive shaft assembly 30 includes axle 76 and gear 78. The axle includes first end 116 and second end 118 and spans across cylinder 20 from the first end thereof to the second end thereof. Gear 78 is positioned substantially perpendicularly relative to the axis of axle 76 proximate second end 118 thereof. Gear 78, in the embodiment shown, includes shoulder 120. As will be explained, shoulder 120 serves to preclude the egress of paste into gear 78, and likewise interfaces with interfacing lip 72 to retain the drive shaft assembly in the desired orientation.

It will be understood that gear 78 is not limited to any particular configuration and may comprise a variety of different gear profiles (straight, angled, beveled, hypoid, etc.) having a varying number of teeth. Preferably, gear 78 and axle 76 are integrally molded from a plastic material, however, both integrated and separate components made from a variety of different materials (metal, alloys thereof, composites, etc.) through a variety of forming processes are likewise contemplated for use.

Cup shaft assembly 32 is shown in FIG. 6 as comprising axle 80, gear 82, lower shoulder 84, and prophy cup 86. Axle 80 includes first end 122, second end 124, and bore 126 extending from first end 122 to second end 124. Axle 80 is positioned within cavity 112 of head portion 22 extending from top end 60 to bottom end 62 thereof. Gear 82 is positioned along axle 80 such that gear 82 and gear 76 interface and mesh. Lower shoulder 84 is associated with second end 124 and is dimensioned so as to correspond to opening 68 of head portion 22.

Prophy cup 86 is shown in FIG. 6 as including outer shoulder 130 and opening 132. Shoulder 130 defines cavity 136 which is capable of storing polishing paste. Shoulder 130 is substantially flexible and may include varying surface configurations within cavity 136 so as to facilitate the polishing of teeth. Opening 132 is in fluid communication with bore 126 extending through axle 80 and with cavity 136 of the prophy cup. Preferably, prophy cup 86 can be co-molded with cup shaft assembly 32 to decrease costs and assembly procedures. As such, prophy cup 86 preferably comprises a flexible material such as a natural or silicone rubber. Of course, other materials are likewise contemplated for use.

Paste feed assembly 16 is shown in FIGS. 3, 4, 6, and 8 as comprising piston assembly 38 and piston movement assembly 40. The paste feed assembly is configured to force paste housed within cylinder 20, ultimately, to prophy cup 86. As shown in more detail in FIGS. 6 and 8, piston assembly 38 includes first end 88, second end 90, outer seal 92, front face 94, trailing surface 96, and bore 98. Front face 94 is positioned proximate second end 90 of piston assembly 38 and substantially follows the cross-sectional configuration of cylinder 20. Outer seal 92 extends about the perimeter of front face 94 and is in slidable engagement with inner surface 54 of cylinder 20. Preferably, the slidable engagement of the outer seal and the inner surface of the cylinder is substantially fluid tight and provides some resistance to such slidable movement.

Trailing surface 96 of piston assembly 38 is shown in greater detail as including plurality of teeth 128. Each of teeth 128 includes forward surface 150 and rearward surface 152. Forward surface 150 is inclined relative to longitudinal axis 133 of the piston assembly at an angle $\alpha$. Similarly, rearward surface 152 is inclined relative to longitudinal axis 133 of the piston assembly at an angle $\beta$. Angle $\alpha$ is approximately 45 degrees, whereas angle $\beta$ is approximately 90 degrees. As will be explained below, the configuration of the teeth permits movement of the fingers only in one direction relative to the trailing surface.

Figure 8:
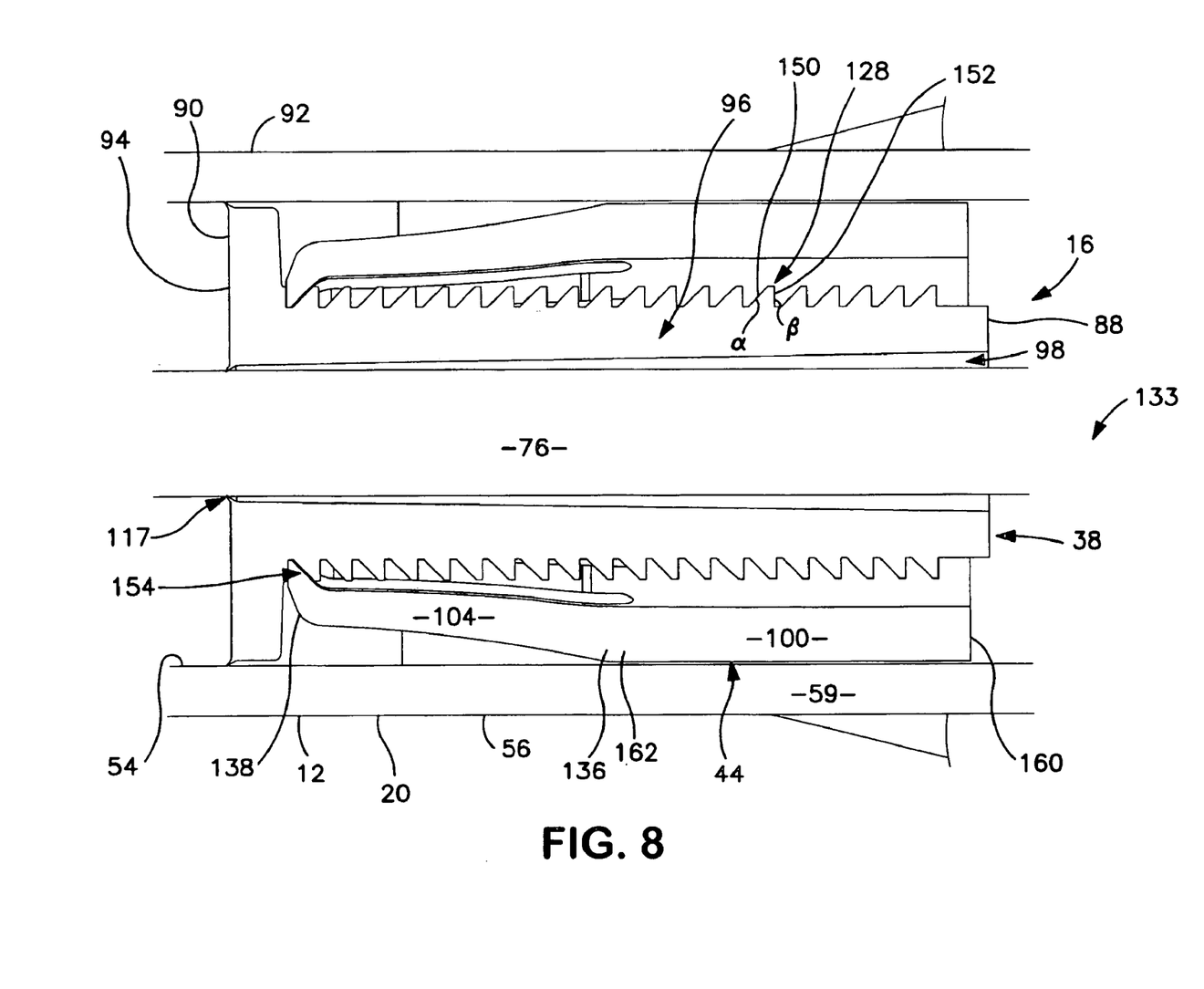
FIG. 8 of the drawings comprises a partial cross-sectional view of a dental apparatus in accordance with the present invention, taken about lines A—A of FIG. 5.

As shown in FIGS. 6 and 8, bore 98 extends from front face 94 through trailing surface 96 substantially along longitudinal axis 133 thereof. Bore 98 includes seal 117 which substantially precludes the passage of paste into bore

98. Bore 98 has a cross-sectional area which substantially corresponds to the cross-sectional configuration of axle 76 of drive shaft assembly 30. As such, axle 76 is capable of substantially freely rotating within bore 98 and piston assembly 38 is capable of substantially freely translating relative to axle 76, yet the passage of paste therein is precluded by seal 117.

Piston movement assembly 40 is shown in FIGS. 3 and 4 as comprising piston engagement member 44 and user activation member 46. The piston movement assembly is configured to move piston assembly 38 from a first position distally spaced from second end 52 of cylinder 20 to a second position which is closer to second end 52 of cylinder 20, in predetermined increments. In turn, any paste 200 (FIG. 4) positioned within the space between front face 94 and second end 52 of cylinder 20 will be forced through the respective passages and into prophy cup 86.

As shown in FIGS. 6 and 8, piston engagement member 44 includes tube member 100, opposing followers (such as follower 102), and teeth engagement fingers 104. Tube member 100 includes first end 160 and second end 162. Generally, tube member 100 is dimensioned so as to substantially correspond with the cross-sectional configuration of cylinder 20, to, in turn, be slidably movable therewithin. Follower 102 comprises profile 134. In this particular embodiment, profile 134 comprises a substantially linear profile, angularly disposed upon tubular member 100 relative to longitudinal axis 133 of the piston assembly. It will be understood that an additional follower is located on the tube member on the side opposite of follower 102, and may comprise an additional profile.

As shown in FIGS. 6 and 8, teeth engagement fingers, such as tooth engagement finger 104, each include proximal end 136 associated with tube member 100, and distal end 138. Gripping teeth 154 are associated with distal end 138 of the teeth engagement fingers and are capable of engaging teeth 128 of trailing surface 96. Each tooth engagement finger 104 is flexible enough to permit elastic outward deformation. Gripping teeth 154 and trailing surface 96 of the piston assembly form a ratchet and pawl mechanism wherein the movement of the gripping teeth toward second end 52 of cavity 20 serves to move the piston assembly in the same direction, while movement of the gripping teeth away from the second end of cavity 20 deforms the gripping teeth to disengage tooth 128 of the piston assembly, and engage an adjoining tooth. In turn, piston assembly 38 remains substantially in place while gripping teeth 154 move in the second direction, namely away from second end 52 of cylinder 20. While a plurality of teeth 128 and gripping teeth 154 are shown in the drawings, the invention is not limited to any particular number of teeth.

User activation member 46 is shown in FIG. 6 as comprising handle 106, biasing member 108, and cam assembly 110. Handle 106 includes first end 140, second end 142, and pivot 144 positioned therebetween. The handle member is disposed on cylinder 20 of body 12 such that pivot 144 interfaces with cylinder 20. Biasing member 108 interfaces to retain the handle member in a desired orientation via pivot 144 which protrudes between handle member 106 and body 12. The user is capable of manipulating handle 106 to, in turn, overcome the biasing means and rotate the handle member about the pivot. Once the user releases the handle, the handle returns to the original orientation by force exerted by the biasing means. The handle member extends away from body 12 so that the distance from first end 140 and pivot 144 is greater than the distance from second end 142 and pivot 144. In turn, the handle member can provide the user with a mechanical advantage, which, in turn, facilitates the advancement of pastes having a variety of different viscosities. In such an embodiment, the handle member is substantially linear. Additionally, due to the size of the handle member, the user can easily move the handle member while utilizing the device, generally, regardless of the position of the prophy angle in the user's hand.

Figure 10:
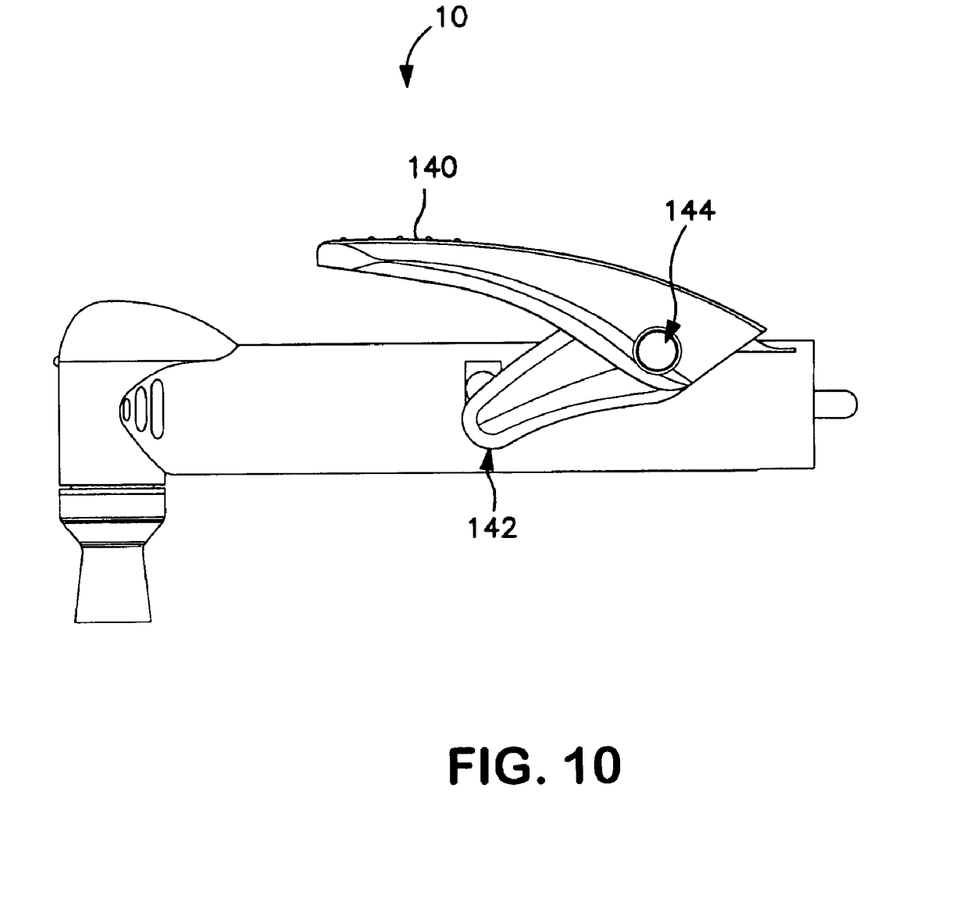
FIG. 10 of the drawings comprises a side elevational view of a dental apparatus in accordance with the present invention.

In another embodiment of the invention, the handle member may have the configuration as shown in FIG. 10. In such an embodiment, the handle member is such that that the leg between first end 140 and pivot 144 is disposed at an angle relative to the leg between second end 142 and pivot 144. Regardless of such an angle, the distance between first end 140 and pivot 144 is greater than the distance between second end 142 and pivot 144. Again, the user is provided with a mechanical advantage such that paste can be driven by the user through activation of the handle regardless of the viscosity of the paste.

As shown in FIG. 6, cam assembly 110 includes opposing arms 146, 146' each having respective cam surfaces 148, 148' positioned on the ends thereof. The cam surfaces are positioned about the distal end of the respective arms and extend through respective slots, such as slot 143 of cylinder 20 (FIGS. 1 and 2), and, in turn, engage respective follower profiles. As will be understood, movement of the handle moves the cam assembly relative to cylinder 20 and relative to follower 102, and, in turn, imparts selective, incremental movement to the piston assembly.

Figure 1:
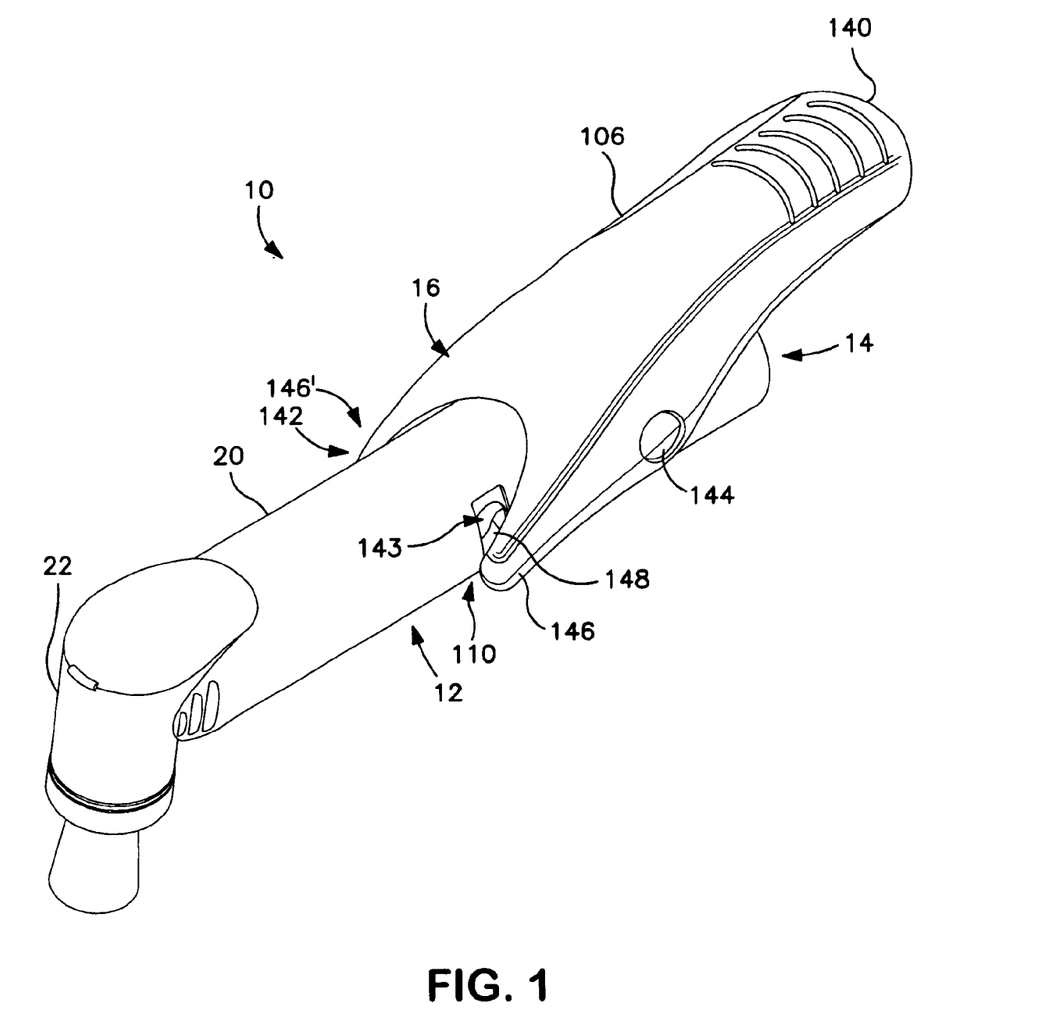
FIG. 1 of the drawings comprises a perspective view of a dental apparatus in accordance with the present invention.
Figure 2:
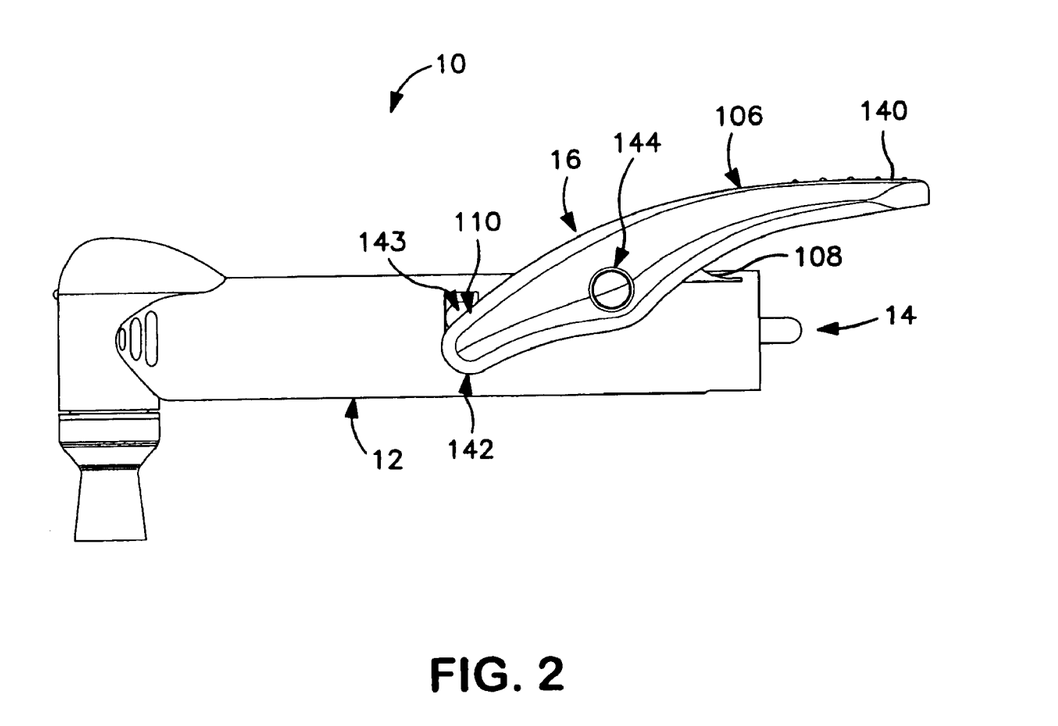
FIG. 2 of the drawings comprises a side elevational view of a dental apparatus in accordance with the present invention.

To assemble prophy angle 10, body 12 is supplied. Specifically, and as shown in FIG. 1, the body comprises an integrated cylinder 20 and head portion 22. As is shown in FIG. 6, once provided, cup shaft assembly 32 is inserted into head portion 22 of body 12. The cup shaft assembly is positioned such that bore 126 of axle 80 is in communication with bore 66 of head portion 22.

Once positioned, piston assembly 38 is mated with piston engagement member 44 such that distal end 138 of teeth engagement fingers 104 substantially correspond with teeth 128 proximate the junction trailing surface 96 and front face 94. Next, axle 76 is directed through bore 98 of piston assembly 38.

Once the piston assembly and the axle have been interfaced, the assembly is inserted into cylinder 20. Axle 76 is directed into cylinder 20 until gear 78 interfaces with gear 82 of cup shaft assembly axle 80. The assembled piston assembly and piston engagement member 44 are slidably moved along bore 98 until the followers 102, 102' located on tube member 100 align with slots 143, 143'.

Next, cap 24 is positioned such that slots 114 and tabs 115 of attachment assembly 74 matingly engage. When matingly engaged, passage 70 is in fluid communication with bore 66 of head portion 22 and second end 52 of cylinder 20. In addition, interfacing lip 72 is positioned such that it cooperates with shoulder 120 of gear 78 to maintain the drive shaft assembly in the desired assembled position.

Subsequently, handle 106 is provided. In particular, the handle is attached to the device by extending opposing cam surfaces, such as cam surface 148, through opposing slots 143 and into respective follower profiles 134.

Finally, the dental paste is driven through prophy cup 86, bore 126 of axle 80, bore 66 of head portion 22, and passage 70 of cap 24 into the area defined by front face 94 of piston assembly 38, inner surface 54 of cylinder 20, and second end 52 of cylinder 20. The particular quantity of paste that is inserted into this area can be varied. Additionally, it is contemplated that the paste may be introduced into cylinder 20 prior to the affixation of cap 24 over head portion 22 of body 12. Once fully assembled, prophy angle 10 is generally packaged into a cellophane, vinyl, or other synthetic bag or container and sealed until use.

In operation, the dental hygienist or practitioner first removes prophy angle 10 from the synthetic bag or container. Next, as shown in FIG. 8, the prophy angle is placed upon the end of dental hand piece 400 conventionally available in the dental office. In particular, first end 50 of cylinder 20 is associated with the dental hand piece. In addition, first end 116 of axle 76 is associated with the drive system of the hand piece. Conventionally, the dental practitioner can control the rotation of axle 76 by way of a hand switch or foot pedal.

Figure 7A:
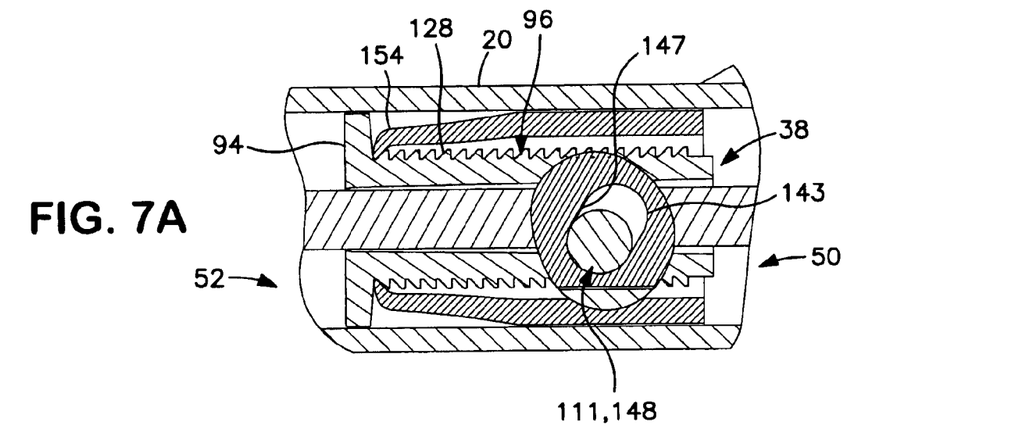
FIGS. 7A through 7F of the drawings each comprise a partial cross-sectional view of a dental apparatus in accordance with the present invention, portions of which are taken about lines A—A of FIG. 5 and portions of which are taken about lines B—B of FIG. 5.
Figure 7B:
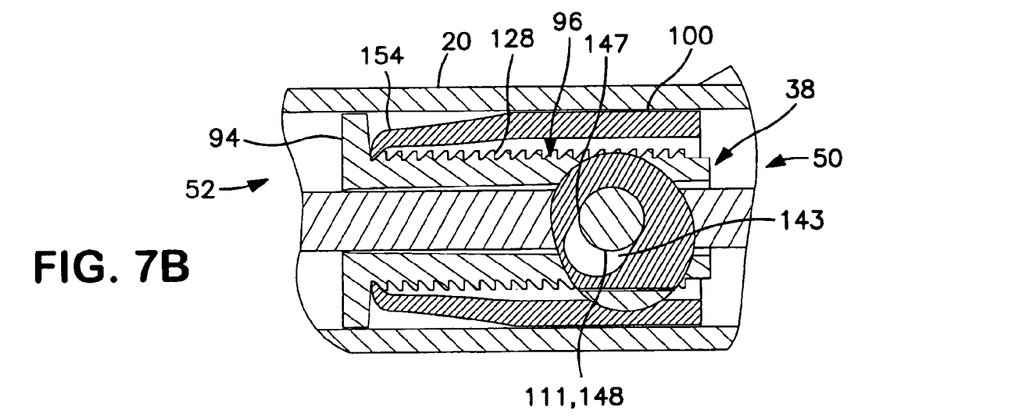

As shown sequentially in FIGS. 7A through 7F, once properly attached to the device, the user can direct paste into prophy cup 86. Initially, the device is in position as depicted in FIG. 7A. To initiate the cycle, the user depresses first end 140 (FIG. 6) of the handle member so as to overcome the biasing means and so as to rotate the handle member relative to the pivot point. As shown in FIG. 7B, cam surface 148 of cam assembly 110 is directed along slot 143, and along profile 134 of follower 102 (FIG. 1). As the cam surface passes detent 147 positioned along slot 143, the user is provided with tactical feedback that the end of the stroke has been reached.

With particular reference to FIG. 7B, as the cam surface is directed along profile 134 of the follower, tube member 100 is directed toward second end 52 of cylinder 20. Gripping teeth 154 associated with tube member 100 engage respective teeth 128 of trailing surface 96 of piston assembly 38, and move piston assembly 38 within cylinder 20 toward second end 52 thereof. In turn, the volume within cylinder 20, between front face 94 and second end 52, is compressed. As will be understood with reference to FIG. 6, such movement of the components directs the paste positioned therein from cylinder 20 through passage 70, bore 66, and bore 126, into prophy cup 86.

Referring now to FIGS. 7C through 7F, as the user releases the handle member, biasing member 108 rotates the handle in the opposite direction, from the second position to the first position, to, in turn, complete the cycle. At such time, cam surface 148 returns toward the original orientation, pulling tube member 100, through contact with follower 102, toward first end 50 of cylinder 20.

Figure 7C:
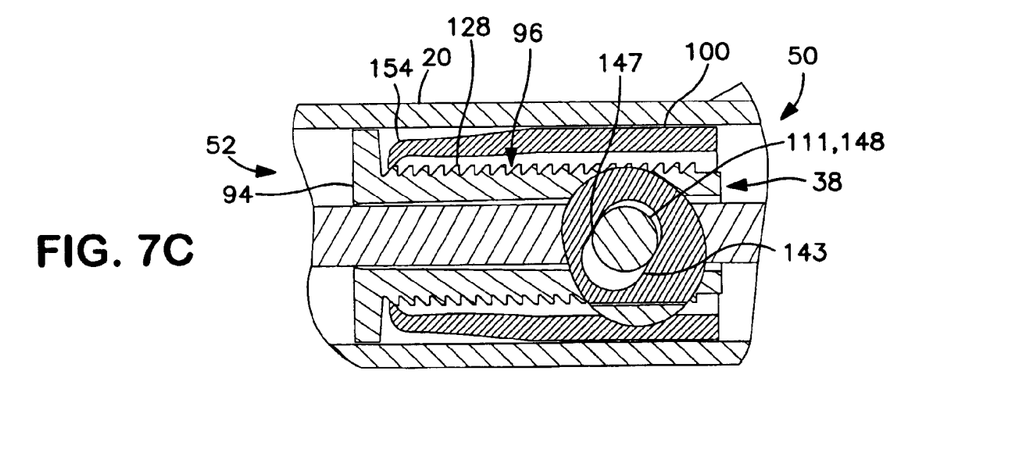
Figure 7D:
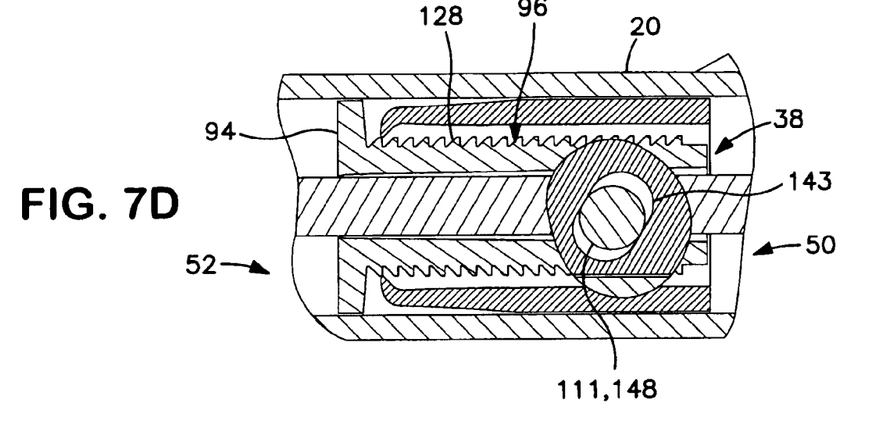

While the handle member (and, in turn, the tube member) returns to the first position, the piston assembly remains substantially stationary. Specifically, the forward surfaces 150 of teeth 128 of trailing surface 96 are inclined at a substantially acute angle. The force required to outwardly plastically deform the distal ends of the teeth engagement fingers (to permit disengagement of the gripping teeth from the forward surface and to permit independent rearward movement of the gripping teeth relative to the trailing surface) is less than the force necessary to overcome the interference fit between outer seal 92 and inner surface 54. Accordingly, when the cam surface of handle 106 directs the tube member, through follower 102, to return to the first position, the piston engagement member and the piston assembly move relative to each other. In turn, as shown in FIG. 7C and 7D, the gripping teeth of the teeth engagement fingers expand and slidably release the tooth to which they are engaged.

Figure 7E:
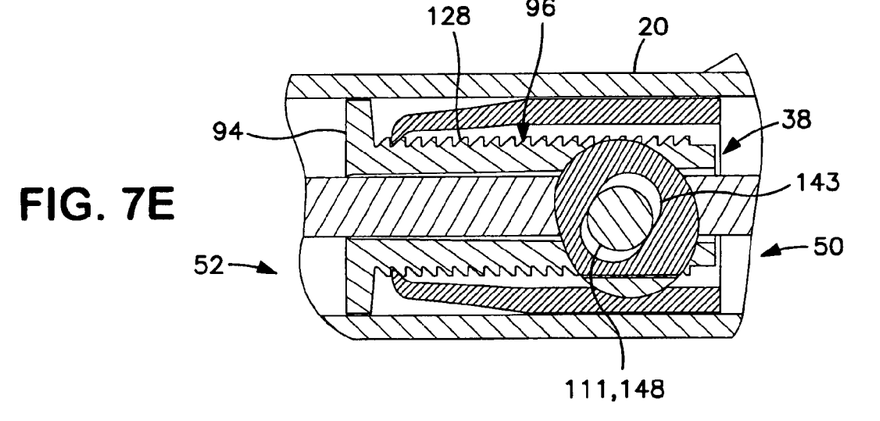
Figure 7F:
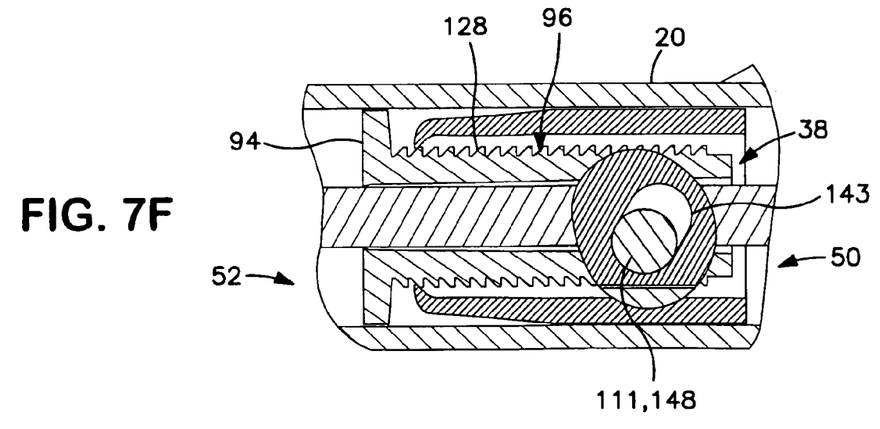

As shown in FIG. 7E, once the tooth has been disengaged, the teeth engagement fingers contract and engage an adjacent tooth of the trailing surface. As shown in FIG. 7F, when the cam follower reaches the first position, the teeth engagement members have progressed a distance along the forward surface 150 of the adjacent tooth.

Due to the construction wherein the teeth spacing is less than the linear distance traveled by the tube member toward second end 52, for each subsequent movement, the teeth engagement members will have progressed a distance along the forward surface of the adjacent tooth a distance substantially equal to the difference between the tooth width and the travel distance of the teeth engagement members during a stroke.

Interestingly, inasmuch as the teeth are at the base of the forward surface of the initial tooth, the travel of the piston assembly during the first cycle will be greater than for subsequent cycles, and will be substantially equal to the linear travel of the tube member toward second end 52 of cylinder 20. This greater travel for the first stroke provides a priming function. Specifically, the first stroke can serve to both place the paste into cup 86 and to substantially eliminate air gaps and other irregularities within the paste such that each subsequent movement stroke will yield a desired amount of paste into the cup.

Subsequent strokes will force a desired amount of material into the prophy cup. In particular, the dimensions of the piston movement assembly may be such that a single actuation fills 50% of the prophy cup. In other embodiments, a single actuation fills 80%, 90%, or 100% of the prophy cup. Indeed, the invention is not limited to any particular dimensions for the piston movement assembly, or any other assembly. Regardless of the actual dimensions, the user can be confident that a proper quantity of paste is dispensed with each actuation, thereby reducing splatter and splashing of the material about the mouth of the patient, as well as about the dental office.

Of course, the teeth size can be varied along the length of the trailing surface. Additionally, it will be understood that the teeth can be sized such that movement of the handle member from the second position to the first position moves the teeth engagement fingers a distance which corresponds to the distance between adjoining teeth of the trailing surface. Throughout this return procedure, the piston assembly remains substantially stationary.

In addition, it is advantageous that a simple actuation of a large and easily grasped handle will correspond to a predetermined quantity of paste being transmitted into the prophy cup. As such, the user can easily refill the prophy cup as desired during the polishing procedure, generally regardless of the orientation of the prophy cup in the dental practitioner's hand, instead of stopping every few strokes to refill the prophy cup from a separate, small container.

Additionally, the user can be confident that a proper quantity of paste is dispensed with each actuation, thereby reducing splatter and splashing of the material about the mouth of the patient, as well as about the dental office.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A prophy angle, comprising:
   a body having a cylinder and a head portion associated with the cylinder;
   a drive system extending through the body, the drive system including:

a drive shaft assembly extending through the cylinder; and a cup shaft assembly extending through the head portion and coupled to the drive shaft assembly, the cup shaft assembly further including a prophy cup disposed at one end thereof, the prophy cup in fluid communication with the body; and a paste feed assembly including:

a piston assembly disposed within the body comprising a front face and a trailing surface, the trailing surface further including a plurality of teeth; and a piston movement assembly including a handle member, the handle member comprising:

a second end associated with the piston assembly, a first end distally spaced therefrom and a pivot point positioned therebetween, wherein a rotation of the first end of the handle member about the pivot point rotates the second end, moving the piston assembly relative to the body, to, in turn, direct a paste positioned within the body to the prophy cup;

the piston movement assembly further includes a piston engagement member, the piston engagement member further including at least one tooth engagement finger, the at least one tooth engagement finger capable of engaging at least one tooth of the trailing surface of the piston assembly;

the piston engagement member coupled to the handle member such that movement of the handle member in a first direction imparts movement to the piston engagement member in a first direction, and movement of the handle member in a second direction imparts movement of the piston engagement member in a second direction; and the teeth of the trailing surface and the at least one tooth engagement finger configured such that movement of the at least one tooth engagement finger in a first direction imparts movement of the piston assembly in a first direction, and movement of the at least one tooth engagement finger in a second direction translates the at least one tooth engagement finger relative to the teeth of the trailing surface wherein, the piston engagement member further comprises a tube member from which the at least one tooth engagement finger extends, the tube member further including at least one follower associated therewith; and the handle member further including at least one cam surface associated with the second end thereof, the at least one cam surface interfacing with the at least one follower, to, in turn, impart slidable movement of the piston engagement member within the cylinder of the body.

2. The prophy angle of claim 1, wherein the at least one tooth engagement member further comprises a plurality of teeth engagement members.

3. The prophy angle of claim 1, wherein:

the tube member further includes at least two followers associated therewith;

the handle member further includes at least two cam surfaces associated with the second end thereof, each of the at least two cam surfaces cooperating with a respective follower to, in turn, impart slidable movement of the piston engagement member within the cylinder of the body.

4. The prophy angle of claim 3, wherein the at least two followers are positioned on opposing sides of the tube member.

5. The prophy angle of claim 1, wherein the trailing surface includes a plurality of teeth positioned sequentially along the length thereof, the at least one tooth engagement finger configured such that movement thereof in the second direction translates the at least one tooth engagement finger sequentially from a first tooth to an adjacent tooth in a direction away from the front face of the piston assembly.

* * * * *